(12) United States Patent
Leighow et al.

(10) Patent No.: US 9,934,539 B2
(45) Date of Patent: Apr. 3, 2018

(54) TIMELINE FOR MULTI-IMAGE VIEWER

(75) Inventors: Carla Leighow, Grain Valley, MO (US); Troy Oliphant, Parkville, MO (US); Jim McKee, Kansas City, MO (US); David A. Robaska, Parkville, MO (US); Shane Van Hook, Blue Springs, MO (US); John R. Quick, Parkville, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

(21) Appl. No.: 13/285,839

(22) Filed: Oct. 31, 2011

(65) Prior Publication Data

US 2013/0110543 A1 May 2, 2013

(51) Int. Cl.
*G06Q 50/22* (2018.01)
*G06Q 50/24* (2012.01)
*G06F 19/00* (2018.01)

(52) U.S. Cl.
CPC .......... *G06Q 50/24* (2013.01); *G06F 19/321* (2013.01); *G06Q 50/22* (2013.01); *G16H 30/20* (2018.01)

(58) Field of Classification Search
CPC ....... G06F 19/321; G06Q 50/24; G06Q 50/22
USPC ........................................ 705/2–3
See application file for complete search history.

(56) References Cited

U.S. PATENT DOCUMENTS

| 6,577,311 | B1 | 6/2003 | Crosby et al. | |
|---|---|---|---|---|
| 2009/0192823 | A1* | 7/2009 | Hawkins et al. | 705/3 |
| 2009/0274384 | A1 | 11/2009 | Jakobovits | |
| 2012/0131507 | A1 | 5/2012 | Sparandara et al. | |

OTHER PUBLICATIONS

Welter, Petra, et al. "Combined DICOM and HL7 viewer in support of a bridge from content-based image retrieval to computer-aided diagnosis." Information Technologies in Biomedicine. Springer Berlin Heidelberg, 2010. 145-152.*
First Action Interview Pre-Interview Communication, dated Sep. 17, 2014, in related U.S. Appl. No. 13/285,847, 18 pp.
Final Office Action dated Jan. 30, 2015 in U.S. Appl. No. 13/285,847, 15 pages.
Non-Final Office Action dated Sep. 24, 2015 in U.S. Appl. No. 13/285,847, 20 pages.
Final Office Action dated May 19, 2016 in U.S. Appl. No. 13/285,847, 24 pages.
Non-Final Office Action dated Jun. 15, 2017 in U.S. Appl. No. 13/285,847, 26 pages.

* cited by examiner

*Primary Examiner* — Minnah L Seoh
(74) *Attorney, Agent, or Firm* — Shook Hardy & Bacon, LLP

(57) ABSTRACT

The systems, methods, and GUIs of the present invention not only have the ability to display DICOM and non-DICOM images simultaneously, side-by-side in a single viewer, but also display a timeline corresponding to more than one healthcare study. A selection of more than one healthcare study from different sources, without requiring a single storage repository or single PACS system, is received and a viewer is launched for the selected studies. Any DICOM images are converted to a non-DICOM format such that non-DICOM images from the more than one healthcare study side-by-side in the viewer. A timeline corresponding to more than one healthcare study for a patient is provided. From the timeline, images from different sources can be selected and displayed side-by-side in the viewer in a non-DICOM format.

20 Claims, 7 Drawing Sheets

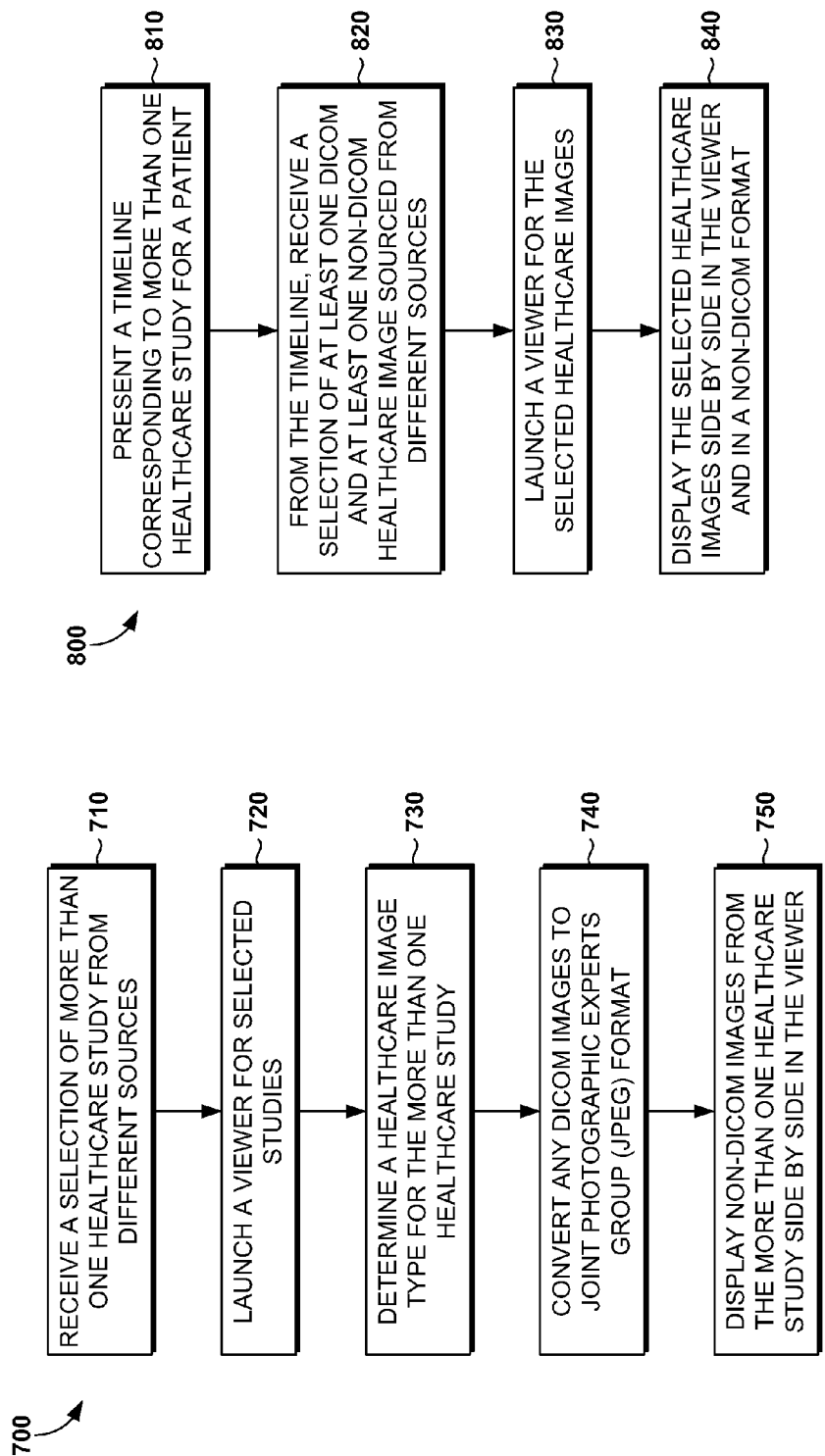

TIMELINE FOR MULTI-IMAGE VIEWER

CROSS REFERENCE TO RELATED APPLICATIONS

This application is related to commonly assigned U.S. Patent Applications entitled "Multi-Image Viewer for Multi-Sourced Images" 13/285,847 filed concurrently herewith on the same date.

BACKGROUND

Oftentimes in a healthcare environment, it is necessary to capture images of a patient. These images can include radiology images, laboratory images, pictures, cardiology images and a variety of other images. These images can be captured electronically in a variety of ways and are used for treatment of the patient. Patient information, such as reports for the images, may also be entered and recorded in a health (or clinical) information system.

While patient information is stored in a clinical information system, the captured images are stored in an archive. Picture archiving and communication systems (PACS) are exemplary digital archives for storing healthcare images, reports, and videos. The captured healthcare images may be stored in a variety of formats including DICOM (Digital Imaging and Communications in Medicine) and non-DICOM objects in native format. In addition, the captured healthcare images are often stored in a variety of locations, depending on the format.

DICOM images are archived according to specific standards for storing, transmitting and handling information in medical imaging. The standards include file format definition and network communications protocol. DICOM groups images together with information such as patient identification so each image is not mistakenly separated from the patient identification. Non-DICOM healthcare images do not adhere to the specific DICOM standards.

Currently, although PACS digital archives can store DICOM, non-DICOM objects in native format, and other storage options, the image viewers to view DICOM and non-DICOM images are separate and DICOM and non-DICOM images cannot be viewed side-by-side within the same viewer. Further, the DICOM and non-DICOM images cannot be accessed from the patient's electronic medical record (EMR). Still further, a clinician is unable to access and view a history of different studies and other clinical images from inside the viewer, making it difficult to understand the entire clinical story associated with the patient.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In one embodiment, one or more computer storage media storing computer-useable instructions that, when executed by one or more computing devices, cause the one or more computing devices to perform a method for displaying at least one DICOM and at least one non-DICOM healthcare image for a patient simultaneously. The method comprises, from an electronic medical record, receiving a selection of more than one healthcare study from different sources. The method further comprises launching a viewer for selected studies. The method further comprises determining a healthcare image type for the more than one healthcare study. The method further comprises converting any DICOM images to Joint Photographic Experts Group (JPEG) format. The method further comprises displaying non-DICOM images from the more than one healthcare study side-by-side in the viewer.

In another embodiment, a computer system for displaying at least one DICOM and at least one non-DICOM healthcare image for a patient simultaneously is provided. The computer system comprises a processor coupled to a computer storage medium, the computer storage medium having stored thereon a plurality of computer software components executable by the processor. The computer software components comprise a selection component for receiving selection of more than one healthcare study from different sources. The computer software components further comprise a viewer component for launching a viewer for the selected studies. The computer software components further comprise a determination component for determining a healthcare image type for the more than one healthcare study. The computer software components further comprise a conversion component for converting DICOM images to JPEG format. The computer software components further comprise a display component for displaying the more than one healthcare image from the more than one healthcare study side-by-side in the viewer and in a non-DICOM format.

In another embodiment, a graphical user interface (GUI) embodied on one or more computer storage medium and executable by a computing device is provided. The GUI comprises a first display area for displaying a list of available multimedia files from more than one source. The GUI further comprises a second display area for displaying selected multimedia files in a non-DICOM format. The GUI further comprises a third display area for displaying other images associated with the selected multimedia files. The GUI further comprises a fourth display area for displaying additional information associated with the selected multimedia files.

In another embodiment, one or more computer storage media storing computer-useable instructions that, when executed by one or more computing devices, cause the one or more computing devices to perform a method for displaying a timeline corresponding to more than one healthcare study. The method comprises presenting a timeline corresponding to more than one healthcare study for a patient. The method further comprises receiving a selection, from the timeline, of at least one DICOM and at least one non-DICOM healthcare image source from different sources. The method further comprises launching a viewer for the selected healthcare images. The method further comprises displaying the selected healthcare images side-by-side in the viewer and in a non-DICOM format.

In another embodiment, a computer system for displaying at least one DICOM and at least one non-DICOM healthcare image is provided. The computer system comprises a processor coupled to a computer storage medium, the computer storage medium having stored thereon a plurality of computer software components executable by the processor. The computer software components comprise a timeline component for presenting a timeline corresponding to more than one healthcare study for a patient. The computer software components further comprise a selection component for receiving, from the timeline, a selection of more than one healthcare image sourced from different sources. The computer software components further comprise a viewer component for launching a viewer for the selected studies. The computer software components further comprise a display component for displaying the more than one healthcare image from the more than one healthcare study side-by-side in the viewer and in a non-DICOM format.

In another embodiment, a graphical user interface (GUI) embodied on one or more computer storage medium and executable by a computing device is provided. The GUI comprises a first display area for displaying a timeline corresponding to more than one healthcare study from more than one source. The GUI further comprises a second display area for displaying selected multimedia files in a non-DICOM format. The GUI further comprises a third display area for displaying additional information associated with the selected multimedia files.

BRIEF DESCRIPTION OF THE SEVERAL VIEWS OF THE DRAWINGS

The present invention is described in detail below with reference to the attached drawing figures, wherein:

FIG. 7 is a flow diagram illustrating a method for displaying at least one DICOM and at least one non-DICOM healthcare image for a patient simultaneously in accordance with an embodiment of the present invention; and FIG. 8 is a flow diagram illustrating a method for displaying a timeline corresponding to more than one healthcare study in accordance with an embodiment of the present invention.

DETAILED DESCRIPTION

Embodiments of the present invention are directed to systems, methods, and GUIs for displaying at least one DICOM and at least one non-DICOM healthcare image for a patient simultaneously. Embodiments of the present invention are also directed to systems, methods, and GUIs for displaying a timeline corresponding to more than one healthcare study. The systems, methods, and GUIs of the present invention not only have the ability to display DICOM and non-DICOM images simultaneously, side-by-side in a single viewer, but also display a timeline corresponding to more than one healthcare study. Having briefly described an overview of the present invention, embodiments of the invention will be discussed with reference to FIGS. 1-8.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Having briefly described embodiments of the present invention, an exemplary operating environment suitable for use in implementing embodiments of the present invention is described below.

Figure 1:
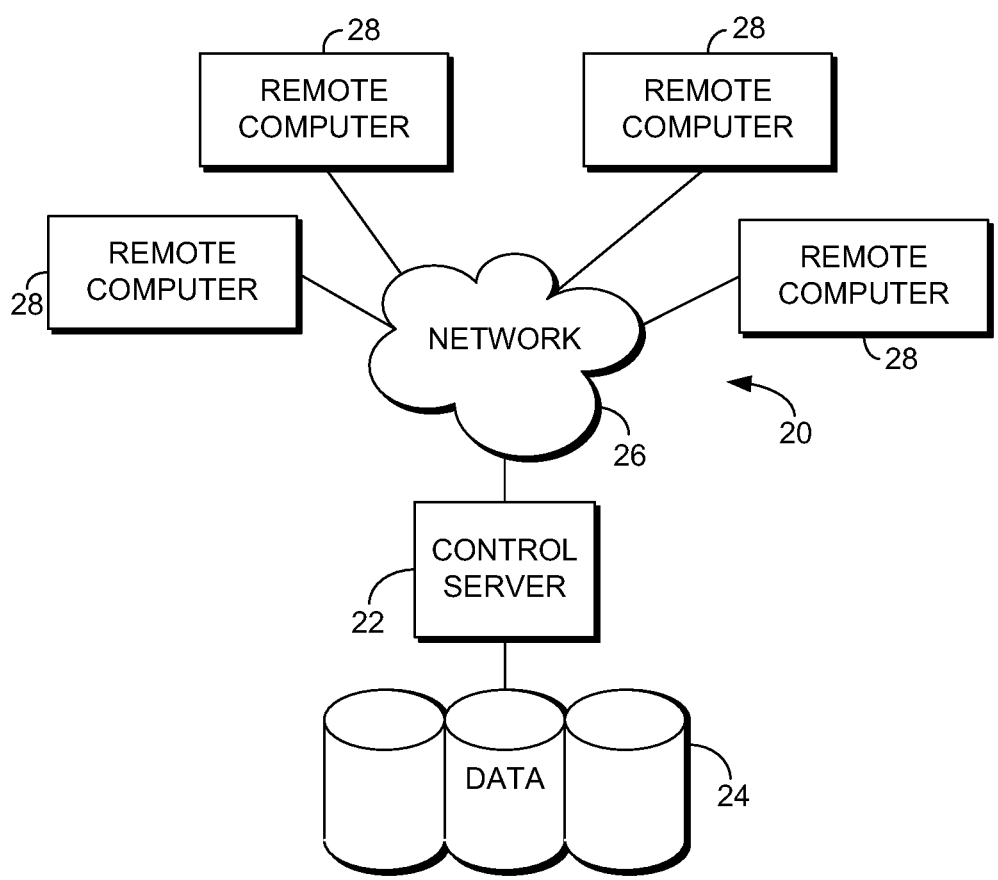
FIG. 1 is a block diagram of an exemplary computing environment suitable for use in implementing embodiments of the present invention.

Referring to the drawings in general, and initially to FIG. 1 in particular, an exemplary computing system environment, a medical information computing system environment, with which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, handheld or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in association with local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer-readable media, for instance, database cluster 24. Computer-readable media can be any available media that may be accessed by server 22, and includes volatile and nonvolatile media, as well as removable and non-removable media. By way of example, and not limitation, computer-readable media may include computer storage media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 22. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 24, provide storage of computer-readable instructions, data structures, program modules, and other data for the control server 22. The control server 22 may operate in a computer network 26 using logical connections to one or more remote computers 28. Remote computers 28 may be located at a variety of locations in a medical or research environment, for example, but not limited to, clinical laboratories (e.g., molecular diagnostic laboratories), hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as intensivists, surgeons, radiologists, cardiologists, and oncologists, emergency medical technicians, physicians' assistants, nurse practitioners, nurses, nurses' aides, pharmacists, dieticians, microbiologists, laboratory experts, laboratory technologists, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the elements described above in relation to the control server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in association with the control server 22, the database cluster 24, or any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., control server 22 and remote computers 28) may be utilized.

In operation, a clinician may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the control server 22. In addition to a monitor, the control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Figure 2:
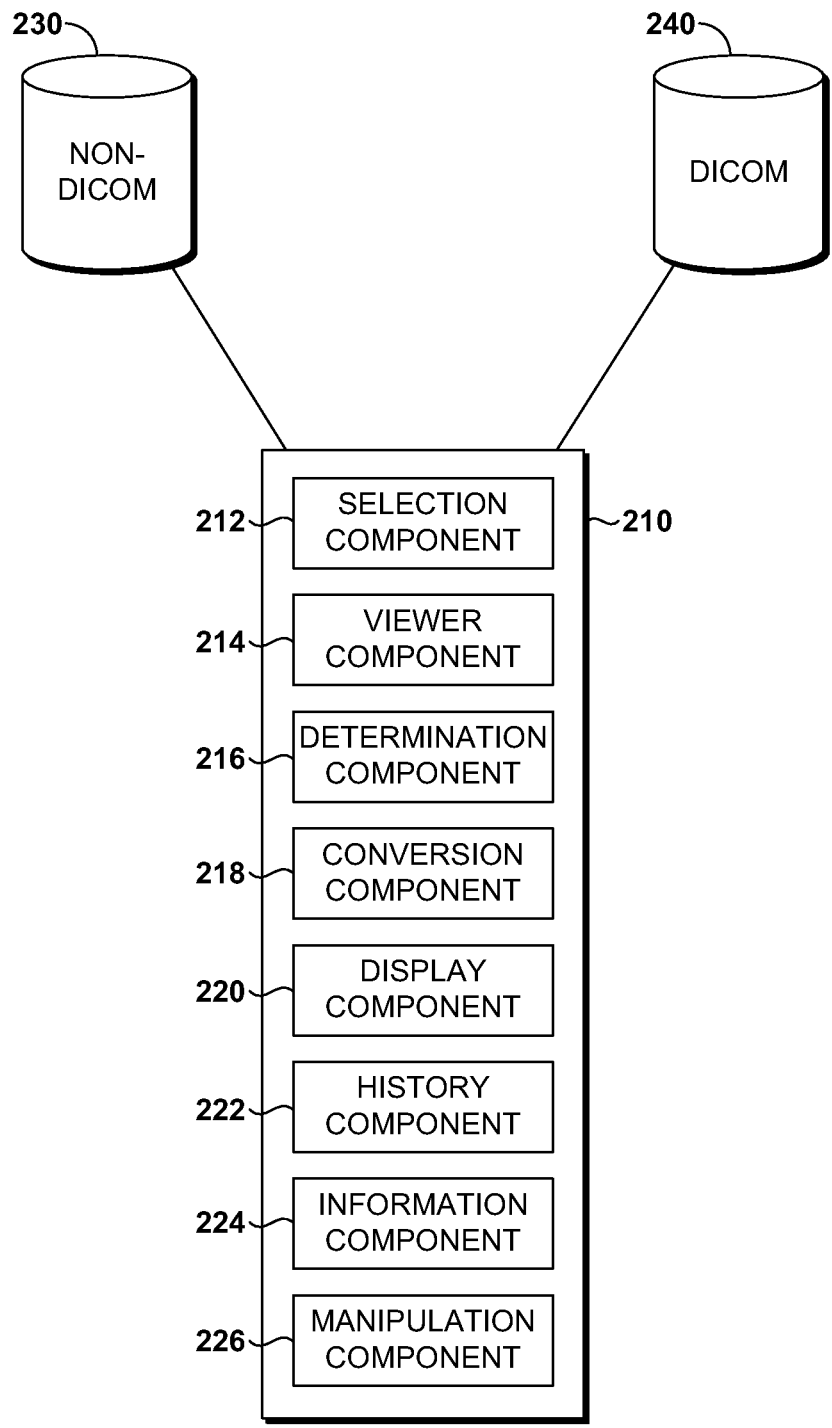
FIG. 2 is an exemplary system architecture suitable for use in implementing embodiments of the present invention.

With reference to FIG. 2, a block diagram is illustrated that shows an exemplary computing system architecture for displaying at least one DICOM and at least one non-DICOM healthcare image for a patient simultaneously. It will be appreciated that the computing system architecture shown in FIG. 2 is merely an example of one suitable computing system and is not intended as having any dependency or requirement related to any single module/component or combination of modules/components.

The computing system includes a multi-image viewer module 210 and one or more databases 230, 240, storing and maintaining non-DICOM and DICOM images. Exemplary non-DICOM and DICOM images include radiology images, laboratory images, pictures, cardiology images, such as ECHO images, and other medical images. One of skill in the art will appreciate that the databases may be maintained separately or may be integrated. Databases 230, 240 may contain images that are linked to a patient's electronic medical record (EMR), such that images may be selected from within the EMR and launched and displayed within a single viewer via the multi-image viewer module 210. As utilized herein, the acronym "EMR" is not meant to be limiting, and may broadly refer to any or all aspects of the patient's medical record rendered in a digital format. Generally, the EMR is supported by systems configured to co-ordinate the storage and retrieval of individual records with the aid of computing devices. As such, a variety of types of healthcare-related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); other images; evidence-based recommendations for specific medical conditions; a record of appointments and physician's notes; billing records; and data received from an associated medical device. Accordingly, systems that employ EMRs reduce medical errors, increase physician efficiency, and reduce costs, as well as promote standardization of healthcare. Graphical display device 220 may be a monitor, computer screen, project device or other hardware device for displaying output capable of displaying graphical user interfaces.

Multi-image viewer module 210 receives and displays images that are sourced from more than one source, or database. Thus, a single storage repository or a single PACS system is not required. Multi-image viewer module 210 may reside on one or more computing devices, such as, for example, the control server 22 described above with reference to FIG. 1. By way of example, the control server 22 includes a computer processor and may be a server, personal computer, desktop computer, laptop computer, handheld device, mobile device, consumer electronic device, or the like.

Multi-image viewer module 210 comprises selection component 212, viewer component 214, determination component 216, conversion component 218, and display component 220. In various embodiments, multi-image viewer module 210 includes a history component 222, an information component 224, and a manipulation component 226. It will be appreciated that while multi-image viewer module 210 is depicted as receiving healthcare images from a single non-DICOM database 230 and a single DICOM database 240, multi-image viewer module 210 may receive healthcare images from multiple non-DICOM, DICOM, and/or mixed sources including databases spread across multiple facilities and/or multiple locations. It will also be appreciated that multi-image viewer module 210 may receives healthcare images from the sources described above via links within a patient's EMR.

The selection component 212 receives a selection of more than one healthcare study. A healthcare study comprises one or more series. For example, the healthcare study may contain a series of images with varying degrees of contrast or a series of images without contrast. Each series comprises one or more images depicting the subject of the image from various angles. A list perspective within a multimedia manager provides a list of available studies, images, and other media. A clinician can select the desired items to launch in the viewer. In one embodiment, the selection of desired items may be made within the EMR.

Once the selection component 212 receives the clinician's selection, the viewer component 214 launches the viewer for the selected studies. The determination component 216 determines a healthcare image type for the more than one healthcare study. That is, the determination component 216 determines whether the healthcare images for each selected study is DICOM or non-DICOM. Any DICOM images are converted to JPEG format by the conversion component 218. This conversion allows non-DICOM and DICOM images to be rendered side-by-side within the same viewer, without DICOM wrapping the non-DICOM images. The display component 220 displays the more than one healthcare study side-by-side in the viewer and in a non-DICOM format.

In one embodiment, a history component 222 displays a history of different studies and clinical images associated with the more than one healthcare image. The history component 222 further allows a selection of one or more images from the history to be displayed in the viewer by the display component 220. For example, the selection component 212 may have received a selection from the clinician of a particular study. However, once the display component 220 has displayed the images that comprise that selected study, the history component 222 may display other studies and clinical images that are of particular interest to the clinician. The clinician may then select additional items from the history to launch within the viewer.

In one embodiment, an information component 224 displays additional information associated with the more than one healthcare image, the history, or a combination thereof. The additional information comprises patient identifying information, image related information, study related information, or a combination thereof. Such additional information may also include time related information.

In one embodiment, a manipulation component 226 allows a clinician to manipulate a display of a healthcare image. For example, a clinician may determine that the image as it is rendered within the viewer is not large enough to see a desired level of detail. The clinician may zoom in or out and the manipulation component 226 manipulates the display of the image accordingly. Similarly, the clinician may desire to pan an image and the manipulation component 226 manipulates the image display accordingly.

Figure 3:
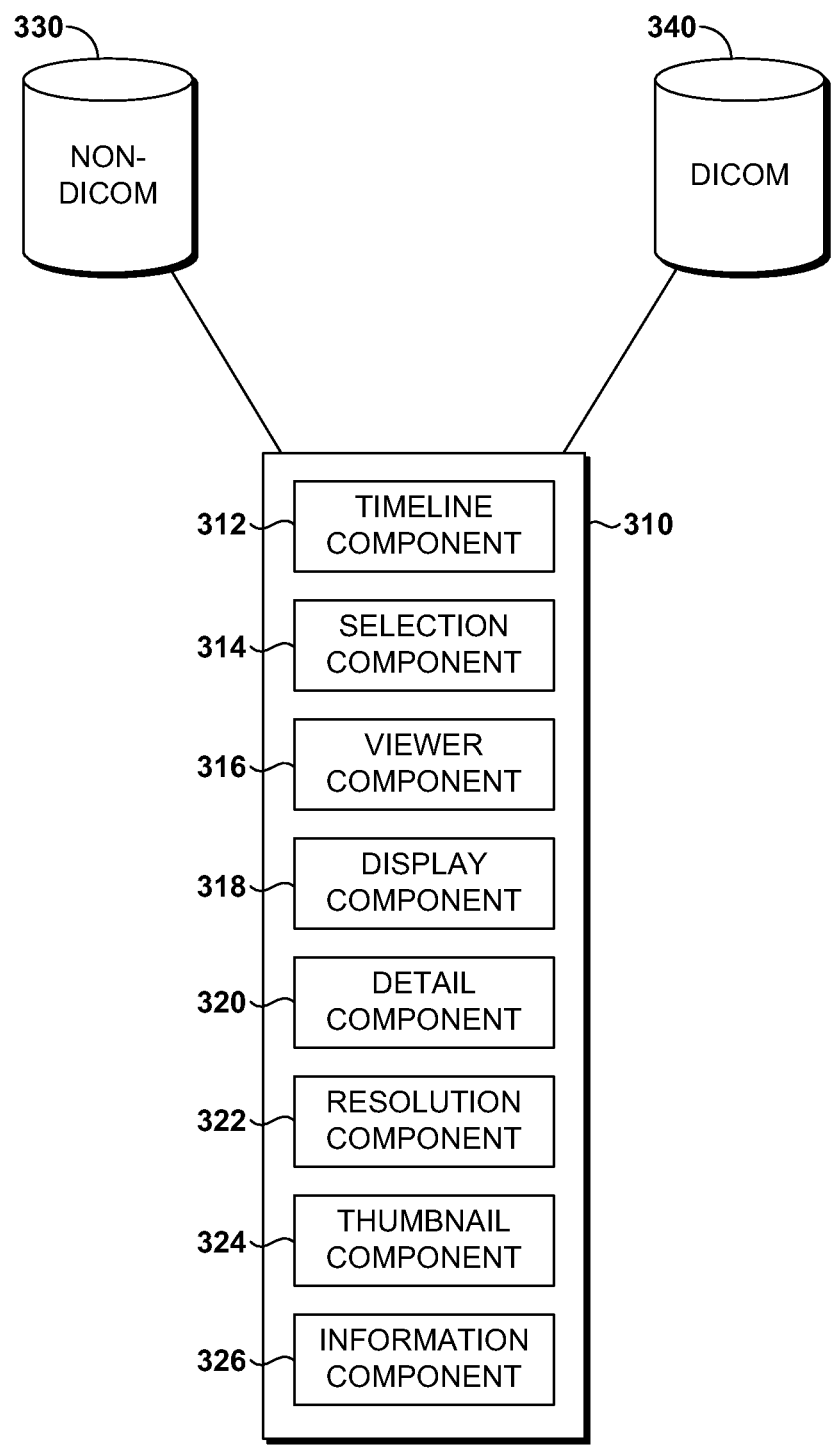
FIG. 3 is an exemplary system architecture suitable for use in implementing embodiments of the present invention.

With reference to FIG. 3, a block diagram is illustrated that shows an exemplary computing system architecture for displaying a timeline corresponding to more than one healthcare study. It will be appreciated that the computing system architecture shown in FIG. 2 is merely an example of one suitable computing system and is not intended as having any dependency or requirement related to any single module/component or combination of modules/components.

The computing system includes a historical module 310 and one or more databases 330, 340, storing and maintaining non-DICOM and DICOM images. As noted above, exemplary non-DICOM and DICOM images include radiology images, laboratory images, pictures, cardiology images, such as ECHO images, and other medical images. One of skill in the art will appreciate that the databases may be maintained separately or may be integrated. Databases 330, 340 may contain images that are linked to a patient's electronic medical record (EMR), such that images may be ordered and displayed in a timeline via the historical module 310.

Historical module 310 receives and displays within in a timeline images that are sourced from more than one source, or database. Historical module 210 may reside on one or more computing devices, such as, for example, the control server 22 described above with reference to FIG. 1. By way of example, the control server 22 includes a computer processor and may be a server, personal computer, desktop computer, laptop computer, handheld device, mobile device, consumer electronic device, or the like.

Historical module 310 comprises timeline component 312, historical selection component 314, historical viewer component 316, and a historical display component 318. In various embodiments, historical module 310 includes a historical detail component 320, a resolution component 322, a thumbnail component 324, and a historical information component 326. It will be appreciated that while historical module 310 is depicted as receiving healthcare images from a single non-DICOM database 330 and a single DICOM database 340, historical module 310 may receive healthcare images from multiple non-DICOM, DICOM, and/or mixed sources including databases spread across multiple facilities and/or multiple locations. It will also be appreciated that historical module 310 may include or incorporate any of the components described above with respect to the multi-image viewer module 210. Similarly, it will be appreciated that the multi-image viewer module 210 may include or incorporate any of the components described above with respect to the historical module 310.

The timeline component 312 presents a timeline corresponding to more than one healthcare study for a patient. For example, after the selection component 212 of the multi-image viewer module 210 receives a selection of more than one healthcare study, the timeline component presents the more than one healthcare study in a timeline. The timeline provides the clinician context for the patient history. Similarly, in one embodiment, the history component 222 of the multi-image viewer module 210 displays other studies and clinical images that are of particular interest to the clinician. These other studies and clinical images are also arranged within the timeline. In one embodiment, a thumbnail component 324 displays at least one thumbnail of an image corresponding to the more than one healthcare study of the timeline. The thumbnails provide a high level view of the image for the event on the timeline to provide a visual of the events associated with the timeline.

A historical selection component 314 receives, from the timeline, a selection of more than one healthcare image sourced from different sources. As described above, the selection includes at least one non-DICOM and one DICOM healthcare image. A historical viewer component 316 launches a viewer for the selected images. A historical display component 318 displays the more than one healthcare image from the more than one healthcare study side-by-side in the viewer and in a non-DICOM format. As described above, any DICOM images are converted to a non-DICOM format, such as JPEG, prior to being displayed by the historical display component 318 within the viewer.

In one embodiment, a historical detail component 320 expands and collapses the timeline to display a level of granularity corresponding to the more than one healthcare study as desired by a clinician. For example, the clinician may desire to see all images associated with a given healthcare study or all images associated with all the healthcare studies appearing on the timeline. The clinician may double click on a healthcare study on the timeline and the historical detail component 320 expands the timeline allowing the clinician to see each image associated with the healthcare study. Or the clinician may indicate, such as with a tool or selecting an appropriate setting, to the historical detail component 320 that the clinician desires to expand the timeline to see all images associated with all healthcare studies appearing on the timeline. Similarly, the clinician may indicate to the historical detail component 320 that the clinician desires to collapse the timeline for a selected healthcare study or for all healthcare studies, such that only the healthcare studies appear on the timeline.

In one embodiment, a resolution component 322 retrieves a DICOM version of an image if a better resolution is desired. For example, the clinician may desire to zoom in on a selected image. The JPEG version of the image may not have the resolution necessary for the clinician to see the desired detail. In this instance, the resolution component retrieves the DICOM version of the image so the desired detail is available for the clinician. In one embodiment, a modified JPEG version of the image is retrieved with the appropriate zoom applied.

In one embodiment, a historical information component 326 includes historical information in the timeline. For example, the historical information component 326 may include historical information associated with the healthcare studies and images that may be relevant to the clinician. This historical information may include non-image items such as procedure reports, healthcare related visits, and other information that may provide context for the clinician to give the clinician a better understanding of the images provided in the viewer.

Figure 4:
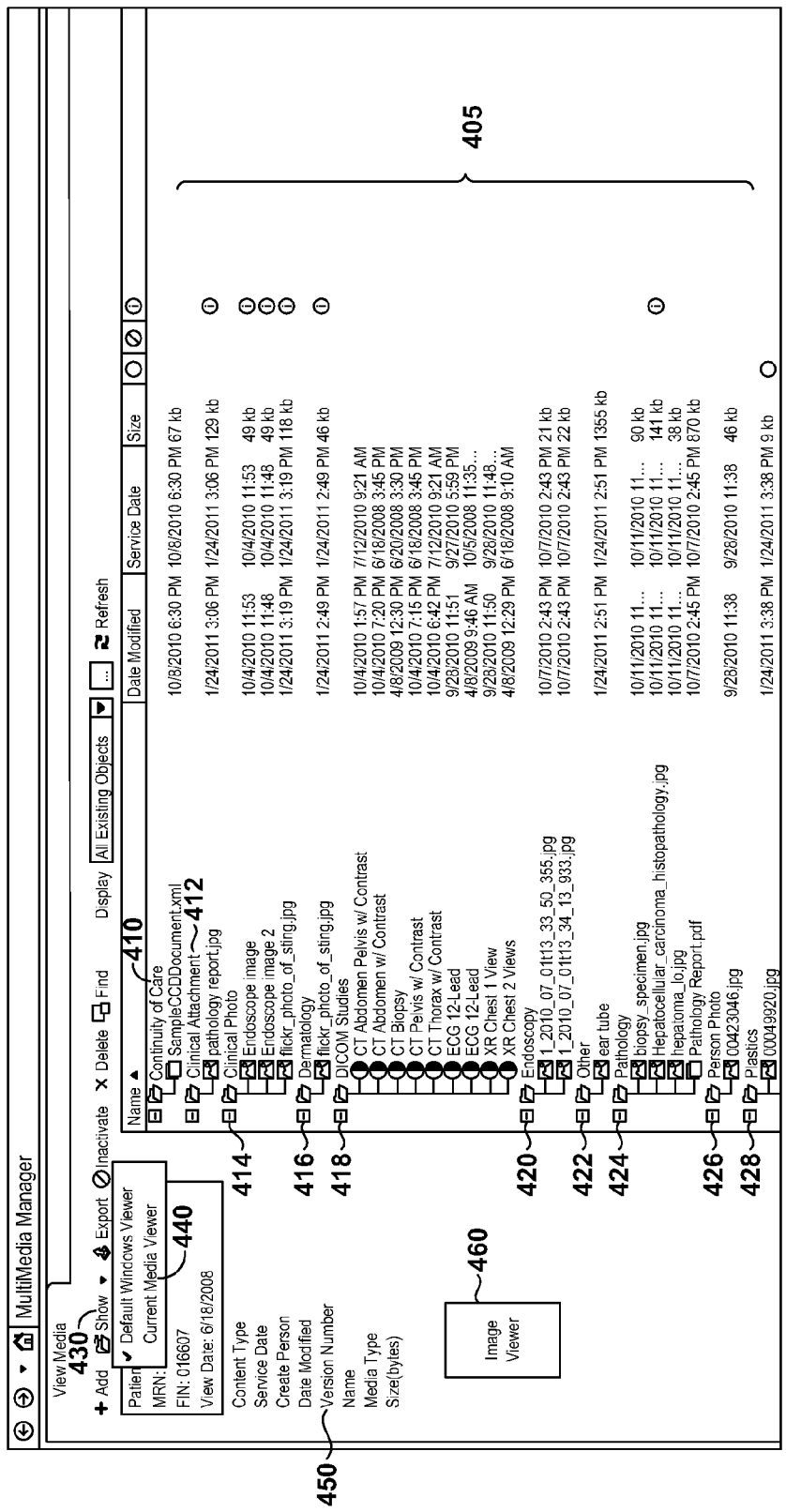
FIG. 4 is an exemplary screen displaying a list of available multimedia files from more than one source in accordance with an embodiment of the present invention.

Referring now to FIG. 4, an exemplary screen displaying a list of available multimedia files from more than one source is shown. A first display area 405 displays a list of available multimedia files from more than one source. Available multimedia files include continuity of care documents 410, clinical attachments 412 (i.e., reports), clinical photos 414, dermatology photos 416, DICOM studies 418, endoscopy photos 420, other photos 422, pathology photos 424, patient photos 426, plastic surgery photos 428, and the like. Information 450 related to the available multimedia files when a particular file is selected and a thumbnail image 460 is shown as a preview to assist the clinician in selecting the desired files. Once the clinician has selected all the desired multimedia files, the clinician can selected the show button 430 and select current media viewer 440 to display the selected files in a single viewer, without DICOM wrapping the images.

Figure 5:
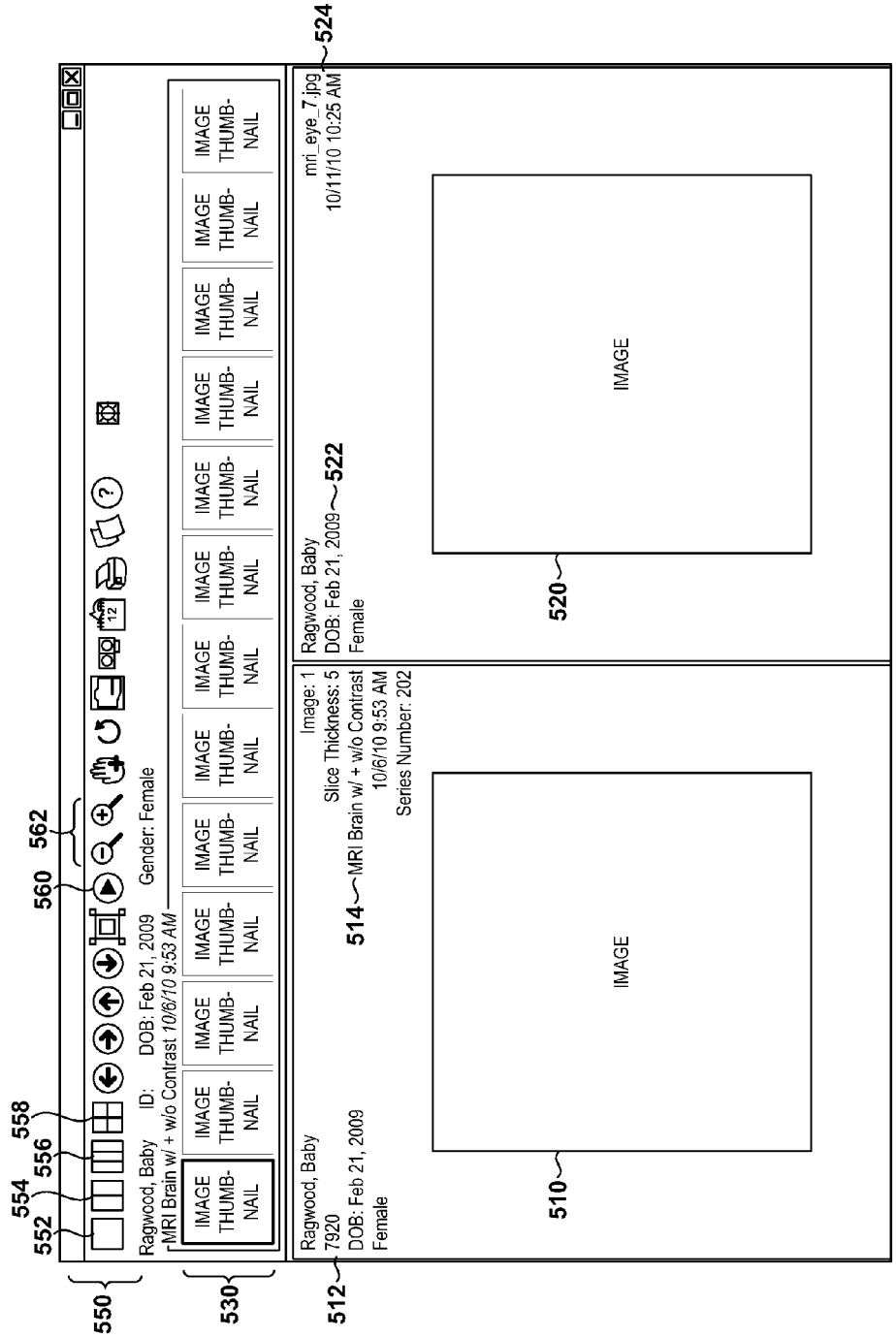
FIG. 5 is an exemplary screen displaying selected multimedia files from more than one source in a non-DICOM format in accordance with an embodiment of the present invention.

Referring now to FIG. 5, an exemplary screen selected multimedia files from more than one source in a non-DICOM format is shown. In various embodiments, the available multimedia files include DICOM and non-DICOM images; however, at least initially, the images are shown in the viewer in a non-DICOM format. A second display area displays selected multimedia files 510, 520 in a non-DICOM format. Thumbnails of images of the selected multimedia files are displayed in a third display area 530, along with previous images associated with the selected multimedia files. The previous images may provide context to a clinician when viewing the images. For example, the previous images may be related to an injury, such as a burn. The images provide a visual story of the patient's recovery and progress and assist the clinician in treating the patient. A fourth display area 512, 514, 522, 524 displays additional information associated with the selected multimedia files for each image displayed by the viewer. The additional information includes patient identifying information, image type, contrast information, date, time, series number, image number, and the like. In one embodiment, a fifth display area displays pathology reports corresponding to the selected multimedia files.

A sixth display area displays tools used for manipulating the selected multimedia files. The tools include a single image tool 552 for showing a single image within the viewer, such as might be desired when a clinician desires to see more detail within a specific image. A two image tool 554 allows the clinician to see two images side-by-side within the viewer. A three image tool 556 and a four image tool 558 allows the clinician to see three or four images, respectively, side-by-side within the viewer. A play tool 560 allows the clinician to play a video file or play through a series of images associated with a particular study. A magnification tool 562 allows a clinician to zoom in and out depending on the level of detail needed.

Figure 6:
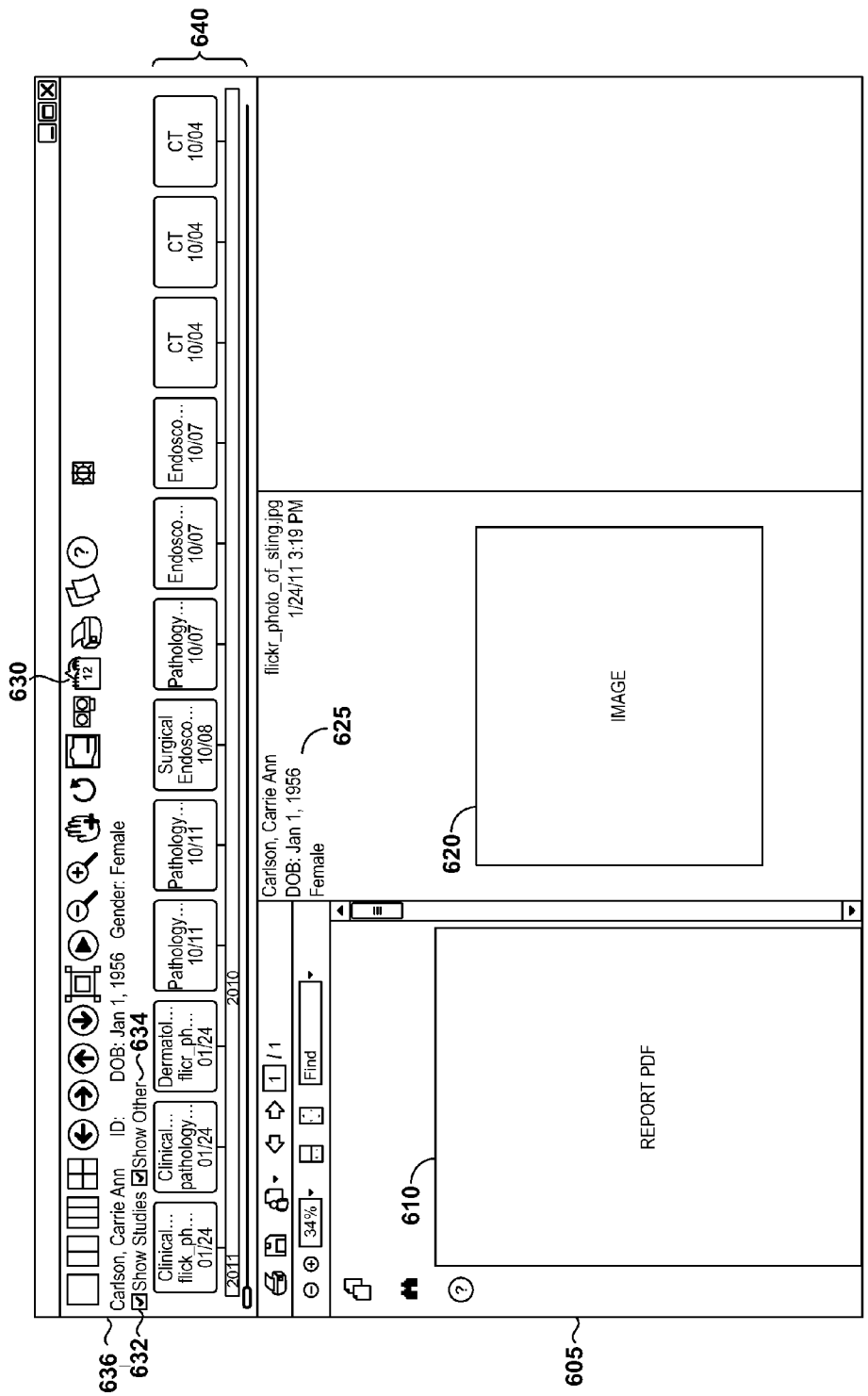
FIG. 6 is an exemplary screen displaying a timeline corresponding to more than one healthcare study from more than one source in accordance with an embodiment of the present invention.

Referring now to FIG. 6, an exemplary screen a timeline corresponding to more than one healthcare study from more than one source is shown. A first display area 640 displays a timeline corresponding to more than one healthcare study from more than one source. A second display area 605 displays selected multimedia files 610, 620 in a non-DICOM format. The multimedia files are, in one embodiment, selected from the timeline. A third display area 636 displays additional information associated with the selected multimedia files. This timeline related information is information related to the timeline as a whole, such as patient identifying information that is the subject of the timeline. In one embodiment, a fourth display area displays at least one thumbnail of an image corresponding to the more than one healthcare study on the timeline. A clinician looking at the thumbnails of the images described above with respect to FIG. 5, may click on the timeline button 630 to display the timeline view. The Show Studies box 632 can be selected to show studies on the timeline and by selecting a study from the timeline, the clinician can view the selected study. Similarly, the Show Other box 634 can be selected and other items appear on the timeline. By selecting an item from the timeline, the clinician can view the selected item. For example, a pathology report may exist for a patient that does not initially appear on the timeline of multimedia files. Once the clinician selects the Show Other box 624, the pathology report may appear on the timeline and is now selectable for viewing inside the viewer side-by-side with the multimedia files. A fifth display area, in one embodiment, displays a history and other clinical images on the timeline. For example, other images related to any selected images, including previous images associated with the selected images, are displayed on the timeline. Once selected by the clinician, these images are rendered inside the viewer along with the selected images. In one embodiment, a sixth display area 625 displays study information. This information is related to the study, or image of a study, that is depicted inside the viewer. Study information comprises patient information, study type, procedure, an indication of contrast, or any combination thereof.

Referring now to FIG. 7, a flow diagram illustrating a method 700 for displaying at least one DICOM and at least one non-DICOM healthcare image for a patient simultaneously is shown. At step 710, a selection of more than one healthcare study from different sources is received. In one embodiment, the more than one healthcare study comprises DICOM and non-DICOM images. In one embodiment, each study comprises one or more series. For example, the study may include a series of images with varying degrees of contrast or a series of images without contrast. In one embodiment, each series comprises one or more images. For example, each series comprises one or more images depicting the subject of the image from various angles.

A viewer is launched, at step 720 for the selected studies. A healthcare image type is determined for the more than one healthcare study at step 730. Any DICOM images are converted, at step 740, to Joint Photographic Experts Group (JPEG) format. At step 750, the non-DICOM images are displayed from the more than one healthcare study side-by-side in the viewer.

In one embodiment, a DICOM version of the images is retrieved if a better resolution is desired. For example, the clinician may desire to zoom in or out on a particular image. If a level of zoom is desired that is beyond the capability of the resolution of the image in the viewer, the DICOM version of the image is retrieved allowing the clinician to zoom in for greater detail. In one embodiment, a modified JPEG version of the image is retrieved with the appropriate zoom applied.

In one embodiment, a history for the patient is provided. In one embodiment, the history for the patient comprises previous images associated with the more than one healthcare image. In another embodiment, the history of the patient includes additional information associated with the more than one healthcare image, the previous images, or a combination thereof. In another embodiment, the history for the patient comprises both the previous images and the additional information. In one embodiment, the additional information comprises reports, studies, patient information from the electronic medical record, or a combination thereof. The history allows the clinician to better understand the context surrounding a given image. In one embodiment, the history is presented in a predefined order. For example, the predefined order may be according to the time and date associated with the history.

In one embodiment, a history of different studies and clinical images associated with the more than one healthcare image is accessed. For example, a clinician may be reviewing an x-ray of a patient. Previous x-rays may be associated with the x-ray the clinician is currently reviewing. The previous x-rays will also be presented to the clinician to provide the clinician with a better understanding of the context surrounding the x-ray. In this example, the context may inform the clinician that a fracture is or is not healing properly.

In one embodiment, thumbnails are retrieved representing each series associated with the more than one healthcare study. These images are presented to the clinician and allow the clinician to select specific images the clinician desires to view within the viewer. These images may be part of the history described above.

Referring now to FIG. 8, a flow diagram illustrating a method 800 for displaying a timeline corresponding to more than one healthcare study is shown. At step 810, a timeline corresponding to more than one healthcare study for a patient is presented. In one embodiment, each study comprises one or more series. In one embodiment, the more than one healthcare study comprises DICOM and non-DICOM images. In one embodiment, each study comprises one or more series. For example, the study may include a series of images with varying degrees of contrast or a series of images without contrast. In one embodiment, each series comprises one or more images. For example, each series comprises one or more images depicting the subject of the image from various angles. In one embodiment, thumbnail images corresponding to each series associated with the healthcare study are displayed within the timeline. The thumbnail images provide a high level view of the event associated with the particular healthcare study. In one embodiment, the timeline includes a thumbnail image associated with each series in the more than one healthcare study. In one embodiment, the timeline includes a thumbnail image associated with each image in the one or more series. In one embodiment, the timeline is expandable and collapsible to display a level of granularity corresponding to the more than one healthcare study as desired by the clinician. For example, the clinician may desire to see within the timeline all related healthcare studies, all series in a particular study, or all images in a particular series. Or, the clinician may desire to see other information as defined herein. In such scenarios, it may be desirable to expand the timeline to include such items. Or, the clinician may desire to see only a high level view of the timeline and prefers to see the collapsed view, showing only selected healthcare studies. In one embodiment, the clinician may desire to filter a particular image type (i.e., wound photos, dermatology, etc.) for the timeline.

A selection of at least one DICOM and at least one non-DICOM healthcare image sourced from different sources is received, at step 820, from the timeline. At step 830, a viewer for the selected healthcare images is launched. The selected healthcare images are displayed, at step 840, side-by-side in the viewer and in a non-DICOM format. In one embodiment, a DICOM version of an image is retrieved if specialized tools are needed (i.e., measurement tools, window/leveling, etc.). For example, the clinician may desire to measure a particular item on a selected image. The JPEG version of the image may not have the resolution necessary for the clinician to see or measure the particular item. In this instance, the resolution component retrieves the DICOM version of the image so the particular item can be measured by the clinician.

In one embodiment, an indication from a clinician is received to include other information in the timeline. The other information may include related healthcare studies or information associated with the healthcare studies and images that may be relevant to the clinician. This other information may also include non-image items such as procedure reports, healthcare related visits, and other information that may provide context for the clinician to give the clinician a better understanding of the images provided in the viewer.

The present invention has been described in relation to particular embodiments, which are intended in all respects to illustrate rather than restrict. Alternative embodiments will become apparent to those skilled in the art that do not depart from its scope. Many alternative embodiments exist, but are not included because of the nature of this invention. A skilled programmer may develop alternative means for implementing the aforementioned improvements without departing from the scope of the present invention.

It will be understood that certain features and sub-combinations of utility may be employed without reference to features and sub-combinations and are contemplated within the scope of the claims. Furthermore, the steps performed need not be performed in the order described.

The invention claimed is:

1. One or more computer hardware storage media (the "media") storing computer-useable instructions that, when executed by one or more computing devices, cause the one or more computing devices to perform a method for displaying a timeline corresponding to more than one healthcare study, the method comprising:
presenting a timeline corresponding to more than one healthcare study for a patient;
from the timeline, receiving a selection of at least one DICOM healthcare image and at least one non-DICOM healthcare image sourced from different sources, wherein a DICOM image adheres to a DICOM standard, which includes file format definition, includes network communications protocol, and groups the DICOM healthcare image with a patient identification and other DICOM healthcare images of the patient, and wherein the at least one DICOM healthcare image and the at least one non-DICOM healthcare image cannot be viewed in a same viewer;
launching a viewer for the selected healthcare images;
converting the at least one DICOM healthcare image to a Joint Photographic Experts Group (JPEG) format, wherein the JPEG format is a non-DICOM standard that does not follow the DICOM standard;
displaying both at least one converted DICOM healthcare image and the at least one non-DICOM healthcare image selected from the timeline side-by-side in the viewer in a non-DICOM format;
receiving input requiring a better resolution of the converted DICOM healthcare image;
retrieving the DICOM healthcare image; and
launching a separate DICOM viewer with specialty tools.

2. The media of claim 1, wherein each study comprises one or more series.

3. The media of claim 2, wherein each series comprises one or more images.

4. The media of claim 3, wherein the timeline is expandable and collapsible to display a level of granularity corresponding to the more than one healthcare study as desired by a clinician.

5. The media of claim 1, further comprising displaying within the timeline thumbnail images corresponding to an image associated with a healthcare study.

6. The media of claim 2, wherein the timeline includes a thumbnail associated with each series in the more than one healthcare study.

7. The media of claim 3, wherein the timeline includes a thumbnail associated with each image in the one or more series.

8. The media of claim 1, further comprising receiving an indication from a clinician to include other information in the timeline.

9. A computer system for displaying a timeline corresponding to more than one healthcare study, the computer system comprising a processor coupled to a computer storage medium, the computer storage medium having stored thereon a plurality of computer software components executable by the processor, the computer software components comprising:
a timeline component for presenting a timeline corresponding to more than one healthcare study for a patient;
a historical selection component for receiving, from the timeline, a selection of one or more DICOM healthcare images and one or more non-DICOM healthcare images from different sources, wherein a DICOM image adheres to a DICOM standard, which includes file format definition, includes network communications protocol, and groups the DICOM healthcare image with a patient identification and other DICOM healthcare images of the patient, and wherein the one or more DICOM healthcare images and the one or more non-DICOM healthcare images cannot be viewed in a same viewer;
a historical viewer component for launching a viewer for the selected images;
a conversion component for converting the one or more DICOM images to a non-DICOM format, wherein the non-DICOM format does not follow the DICOM standard;
a historical display component for displaying both one or more converted DICOM healthcare images and one or more non-DICOM healthcare images side-by-side in the viewer in a non-DICOM format; and
a resolution component for retrieving a DICOM version of a healthcare image previously converted from the DICOM format to the non-DICOM format if a better resolution is desired.

10. The system of claim 9, further comprising a historical detail component for expanding and collapsing the timeline to display a level of granularity corresponding to the more than one healthcare study as desired by a clinician.

11. The system of claim 9, further comprising a thumbnail component for displaying at least one thumbnail of an image corresponding to the more than one healthcare study of the timeline.

12. The system of claim 9, further comprising a historical information component for including historical information in the timeline.

13. The media of claim 1, wherein the source for at least one of the DICOM image and the non-DICOM image is received as a link from an EMR for the patient.

14. The media of claim 1, further comprising determining a healthcare image type for the selected images.

15. The media of claim 1, wherein the at least one non-DICOM image does not have DICOM wrapping.

16. The media of claim 1, wherein the input requiring the better resolution comprises zooming in on an image, measuring an item in the image, or leveling the image.

17. The media of claim 1, wherein the different sources include two or more databases from two or more facilities or locations.

18. The media of claim 1, further comprising presenting an option to include non-image files on the timeline.

19. The media of claim 1, wherein DICOM images are converted to JPEG format before displaying the timeline.

20. The media of claim 1, further comprising filtering the timeline based on a particular image type.

\* \* \* \* \*